United States Patent [19]

Zahler et al.

[11] Patent Number: 4,647,660

[45] Date of Patent: Mar. 3, 1987

[54] 3-ACYLAMINO-2-OXO-1-AZETIDINESULFONIC ACIDS

[75] Inventors: Robert Zahler, Princeton, N.J.; Hermann Breuer, Schoenhofen, Fed. Rep. of Germany; Glenn A. Jacobs, Princeton, N.J.

[73] Assignee: E. R. Squibb & Sons, Inc., Princeton, N.J.

[21] Appl. No.: 729,823

[22] Filed: May 2, 1985

[51] Int. Cl.$^4$ ............... C07D 205/08; C07D 401/12; C07D 403/12; C07D 403/04

[52] U.S. Cl. .................. 540/355; 546/309; 548/233; 548/194; 548/337; 548/128; 562/440; 560/35

[58] Field of Search .................. 260/239 A

[56] References Cited

U.S. PATENT DOCUMENTS 4,288,435 9/1981 Kamiya et al. ............... 544/25
4,385,177 5/1983 Foxton et al. ............... 544/25

FOREIGN PATENT DOCUMENTS 2071650 9/1981 United Kingdom .

OTHER PUBLICATIONS

"Abstracts of 1984 ICAAC Meeting", Abstract #646.

Primary Examiner—Mark L. Berch

Attorney, Agent, or Firm—Lawrence S. Levinson; Donald J. Barrack

[57] ABSTRACT

Antibacterial activity is exhibited by 2-azetidinones activated in the 1-position with an —SO$_3$H group and having in the 3-position an acylamino group of the formula

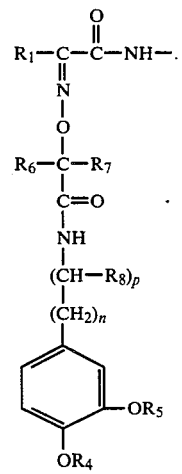

22 Claims, No Drawings

3-ACYLAMINO-2-OXO-1-AZETIDINESULFONIC ACIDS

BRIEF DESCRIPTION OF THE INVENTION

Compounds having the formula

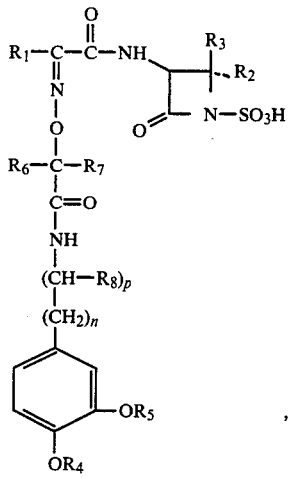

and pharmaceutically acceptable salts thereof, have antibacterial activity. In formula I, and throughout the specification, the symbols are as defined below.

$R_1$ is phenyl, substituted phenyl, 2-amino-4-thiazolyl, 5-amino-3-(1,2,4-thiadiazolyl), 2-amino-oxazolyl, 2-amino-4-imidazolyl, or 2-amino-6-pyridyl;

$R_2$ and $R_3$ are the same or different and each is hydrogen, alkyl, alkenyl, alkynyl, cycloalkyl, phenyl, substituted phenyl or a 4, 5, 6 or 7-membered heterocycle (hereinafter referred to as $R_a$), or one of $R_2$ and $R_3$ is hydrogen and the other is azido, halomethyl, dihalomethyl, trihalomethyl, alkoxycarbonyl, 2-phenylethenyl, 2-phenylethynyl, carboxyl, —CH$_2$X$_1$ [wherein X$_1$ is azido, amino (—NH$_2$), hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

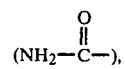

—S—X$_2$, or —O—X$_2$ (wherein A, X$_2$, X$_6$ and X$_7$ are as hereinafter defined)], —S—X$_2$ or —O—X$_2$ [wherein X$_2$ is alkyl, substituted alkyl, phenyl, substituted phenyl, phenylalkyl, (substituted phenyl)alkyl, alkanoyl, phenylalkanoyl, (substituted phenyl)alkanoyl, phenylcarbonyl, (substituted phenyl)carbonyl, or heteroarylcarbonyl],

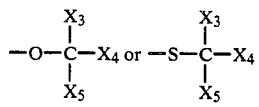

[wherein one of X$_3$ and X$_4$ is hydrogen and the other is hydrogen or alkyl, or X$_3$ and X$_4$ when taken together with the carbon atom to which they are attached form a cycloalkyl group; and X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

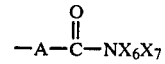

(substituted amino)carbonyl, or cyano (—C≡N)], or

[wherein A is —CH=CH—, —(CH$_2$)$_m$—, —(CH$_2$)$_m$—O—, —(CH$_2$)$_m$—NH—, or —CH$_2$—S—CH$_2$—, m is 0, 1 or 2, and X$_6$ and X$_7$ are the same or different and each is hydrogen, alkyl, phenyl or substituted phenyl, or X$_6$ is hydrogen and X$_7$ is amino, substituted amino, alkanoylamino or alkoxy, or X$_6$ and X$_7$ when taken together with the nitrogen atom to which they are attached form a 4, 5, 6 or 7-membered heterocycle];

$R_4$ and $R_5$ are the same or different and each is hydrogen or alkanoyl;

$R_6$ and $R_7$ are the same or different and each is hydrogen or alkyl or $R_6$ and $R_7$ together with the carbon atom to which they are attached are cycloalkyl;

$R_8$ is $$-\overset{O}{\underset{\|}{C}}-Y_1$$

wherein $Y_1$ is hydroxy, alkoxy, or —NY$_2$Y$_3$ and Y$_2$ and Y$_3$ are the same or different and each is hydrogen or alkyl;

p is 0 or 1; and n is 0, 1, 2 or 3.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "cycloalkyl" refers to cycloalkyl groups having 3,4,5,6 or 7 carbon atoms.

The term "substituted alkyl" refers to alkyl groups substituted with one or more (preferably 1, 2 or 3) azido, amino (—NH$_2$), halogen, hydroxy, carboxy, cyano, alkoxycarbonyl, aminocarbonyl, alkanoyloxy, alkoxy, phenyloxy, (substituted phenyl)oxy, R$_a$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "substituted phenyl" refers to a phenyl group substituted with 1, 2 or 3 amino (—NH$_2$), halogen, hydroxyl, trifluoromethyl, alkyl (of 1 to 4 carbon atoms), alkoxy (of 1 to 4 carbon atoms), alkanoyloxy, aminocarbonyl, or carboxy groups.

The expression "a 4,5,6 or 7-membered heterocycle" (referred to as "$R_a$") refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino

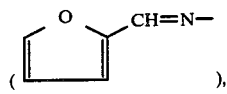

benzylideneamino and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imidazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NX$_8$X$_9$ wherein X$_8$ is hydrogen, alkyl, phenyl, substituted phenyl, phenylalkyl or (substituted phenyl)alkyl, and X$_9$ is alkyl, phenyl, substituted phenyl, phenylalkyl, (substituted phenyl)alkyl, hydroxy, cyano, alkoxy, phenylalkoxy, or amino (—NH$_2$).

The compounds of this invention form basic salts with inorganic and organic bases which are also within the scope of this invention. Such salts include ammonium salts, alkali metal salts, alkaline earth metal salts, and salts with organic bases such as dicyclohexylamine, benzathine, N-methyl-D-gluccamine, hydrabamine and the like.

The compounds of this invention are pictured as acids. They can also exist, however, as zwitterions (internal or inner salts), and these are also included within the language "pharmaceutically acceptable salts" and the scope of this invention.

DETAILED DESCRIPTION OF THE INVENTION

The β-lactams of formula I, and pharmaceutically acceptable salts thereof, have activity against gram-positive and gram-negative organisms. Of particular interest is the good antipseudomonal activity exhibited by the compounds of this invention. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with β-lactams of this invention. Such methods of administration include oral, intravenous, intramuscular, and as a suppository.

The compounds of this invention can be prepared by coupling a compound having the formula

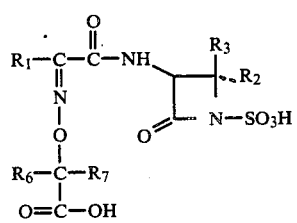

with a nucleophile having the formula

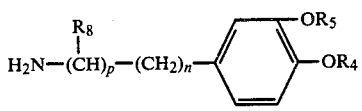

The coupling reaction can be run using procedures well known in the art. Exemplary of such procedures are the dicyclohexylcarbodiimide coupling and thecicyclohexylcarbodiimide/N-hydroxybenzotriazole coupling.

Alternatively, the compounds of this invention can be prepared by condensing a glyoxylic acid having the formula

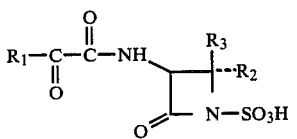

with an alkoxylamine having the formula

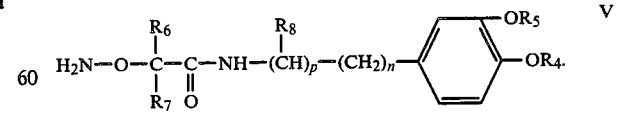

The condensation reaction can be run in water, an organic solvent, or a mixed organic solvent-water system.

A third procedure for preparing the compounds of this invention comprises coupling a carboxylic acid having the formula

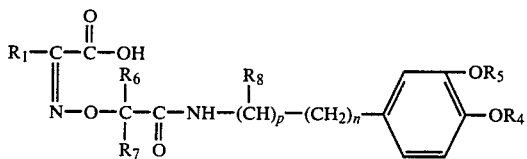

with a β-lactam having the formula

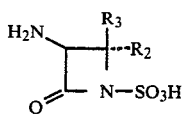

The reaction proceeds most readily if the carboxylic acid is in an activated form. Activated forms of carbbxylic acids are well known in the art include acid halides, acid anhydrides (including mixed anhydrides), activated acid amides and activated acid esters.

The β-lactam of formulas II, IV and VII can be prepared using the methodology described in United Kingdom patent application No. 2,071,650, published Sept. 23, 1981.

A starting material of formula V can be prepared by first reacting a phthalimide having the formula

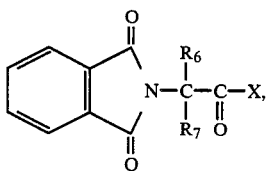

wherein X is a halogen or hydroxyl group, with a compound of formula III. When X is hydroxyl, the reaction proceeds best in the presence of a coupling agent such as dicyclohexylcarbodiimide. The phthalimide protecting group is then removed using hydrazine or methylhydrazine. Amine protecting groups other than the phthalimide group can also be used in preparing a compound of formula V.

A carboxylic acid reactant of formula VI can be prepared by reacting a compound having the formula

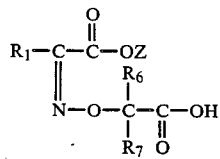

with a compound of formula III. Alternatively, a glyoxylic having the formula

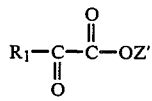

can be reacted with a compound of formula V to yield the desired reactant of formula VI. As used above, the symbol "Z" represents a carboxylic acid protecting group and "Z'" represents hydrogen or a carboxylic acid protecting group. The carboxylic acids of formula VI are an integral part of this invention.

In the above reactions, if the $R_1$ group contains an amino substituent, it may be protected; exemplary protecting groups are the triphenylmethyl and formyl groups. If the $R_8$ group is carboxyl, it may also be protected during the above reactions; exemplary protecting groups are the benzhydryl and benzyl groups.

Those compounds of formula I wherein $R_1$ is 2-amino-4-thiazolyl are preferred. Also preferred, are those compounds wherein $R_4$ and $R_5$ are hydrogen. In the case of $R_6$ and $R_7$, methyl is the preferred alkyl group.

The compounds of formula I contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins (e.g., cephamycin C).

The compounds of formula I have the imino substituent

and can, therefore, exist as the syn or anti isomer or as a mixture of isomers. All of these isomeric forms are within the scope of this invention. In general, however, the syn isomer of a compound of formula I has the greatest activity.

The following examples are specific embodiments of this invention.

EXAMPLE 1

[3S-[3α(Z),4β]]-2-[[[1-(2-Amino-4-thiazolyl)-2-[4-methyl-2-oxo-1-sulfo-3-azetidinyl)amino]-2-oxoethylidene]amino]oxy]-N-(3,4-dihydroxyphenyl)-2-methylpropanamide, monopotassium salt A mixture of [3S-[3α(Z),4β]]-3-[[(2-amino-4-thiazolyl)[(1-carboxy-1-methylethoxy)imino]acetyl]amino]-4-methyl-2-oxo-1-azatidinesulfonic acid (2.18 g, 5.0 mmol), N-hydroxybenzotriazole (676 mg, 5.0 mmol) and triethylamine (697 μl, 506 mg, 5 mmol) was cooled to 0° C. and treated with dicyclohexylcarbodiimide (1.0 g, 5.0 mmol). After stirring for 30 minutes at 0° C. the mixture was added to a cold dimethylformamide solution containing 4-aminocatechol (prepared by hydrogenating 5 mmol of 4-nitrocatechol). The reaction was then allowed to stir overnight at ambient temperature. The dimethylformamide was removed in vacuo, yielding a dark residue which was partially dissolved in 10 ml of water, the pH adjusted to pH 6.5 with potassium bicarbonate solution and then filtered to remove the dicyclohexyl and palladium on charcoal. The aqueous solution was purified on Dowex K⊕ ion exchange resin eluting the column with water. The water was lyophilized yielding 460 mg of the title compound as a tan solid.

Analysis calc'd for $C_{19}H_{21}N_6S_2O_9K.1.75$ mole $H_2O$: C, 37.25; H, 4.04; N, 13.72; S, 10.48. Found: C, 37.25; H, 3.92; N, 13.85; S, 10.28.

EXAMPLE 2

[3S-[3α(Z),4α]]-2-[[[1-(2-Amino-4-thiazolyl)-2-[(4-methyl-2-oxo-1-sulfo-3-azetidinyl)amino]-2-oxoethylidene]amino]oxy]-N-(3,4-dihydroxyphenyl)-2-methylpropanamide, monopotassium salt A mixture of [3S-[3α(Z),4α]]-3-[[(2-amino-4-thiazolyl)[(1-carboxy-1-methylethoxy)imino]acetyl]amino]-4-methyl-2-oxo-1-azetidinesulfonic acid, dipotassium salt (400 mg, 0.78 mmol) and 1 equivalent of p-toluenesulfonic acid (148 mg, 0.78 mmol) was suspended in 2 ml of dry dimethylformamide under an argon atmosphere, and after stirring for 5 minutes had completely dissolved. N-Hydroxybenzotriazole (105 mg, 0.78 mmol) was added to the mixture followed by the addition of dicyclohexylcarbodiimide (161 mg, 0.78 C mmol). After stirring for 30 minutes at room temperature the mixture was added to the dimethylformamide solution containing 4-aminocatechol (prepared by hydrogenating 0.8 mmole of 4-nitrocatechol). The reaction was then allowed to stir overnight at ambient temperature. The dimethylformamide was removed in vacuo, yielding a dark residue which was partially dissolved in 5 ml of water, the pH adjusted to 6.5 with potassium bicarbonate solution and filtered to remove the dicyclohexyl urea and palladium on charcoal. The aqueous solution was passed through a 30 ml Dowex K+ ion-exchange column in water collecting 5 ml fractions. Fractions 4 to 10 were combined and lyophilized to yield 220 mg of semi-pure product. The crude product was purified on a 75 ml HP-20 resin column in water collecting 8 ml fractions. Fractions 55 to 80 were combined and lyophilized to yield 132 mg of the title compound as a tan solid.

Analysis calc'd for $C_{19}H_{21}N_6S_2O_9K.3$ mole $H_2O$ C, 35.82; H, 4.31; N, 13.19; S, 10.06. Found; C, 35.82; H, 4.31; N, 13.01; S, 9.84.

EXAMPLE 3

[3S-[3α(Z),4β]]-2-[[[1-(2-Amino-4-thiazolyl)-2-[(4-methyl-2-oxo-1-sulfo-3-azetidinyl)amino]-2-oxoethylidene]amino]oxy]-N-(3,4-dihydroxyphenyl)-acetamide, monopotassium salt A mixture of [3S-[3α(Z),4β]]-3-[[(2-amino-4-thiazolyl)[(carboxymethoxy)imino]acetyl]-amino]-4-methyl-2-oxo-1-azetidinesulfonic acid, disodium salt (195 mg, 0.4 mmol) and 1 equivalent of p-toluenesulfonic acid (76 mg, 0.4 mmol) was stirred in 1.5 ml of dry dimethylformamide under an argon atmosphere, and after stirring for 5 minutes had completely dissolved. The mixture was added to a dimethylformamide solution containing 4-aminocatechol (prepared by hydrogenating 0.4 mmole of 4-nitrocatechol) followed by the addition of dicyclohexylcarbodiimide (83 mg, 0.4 mmol). The reaction was then allowed to stir overnight at ambient temperature. The dimethylformamide was removed in vacuo yielding a dark residue which was partially dissolved in 5 ml of water, the pH adjusted to 6.5 with potassium bicarbonate solution and filtered to removed the dicyclohexyl and palladium on charcoal. The aqueous solution was passed through a Dowex K+ ion-exchange column in water collecting 8 ml fractions. Fractions 5 to 10 were combined and lyophilized to yield 67 mg of semi-pure product. The crude product was purified on a 30 ml HP-20 resin column eluting with water collecting 5 ml fractions. Fractions 30 to 68 were combined and lyophilized to yield 48 mg of the title compound as a tan solid.

Analysis cal'd for $C_{17}H_{17}Nphd 6S_2O_9K.2.7$ mole $H_2O$: C, 33.97; H, 3.75; N, 13.99. Found C, 33.97; H, 3.74; N, 14.18.

EXAMPLE 4

[3S-[3α(Z),4α]]-4-[[(Aminocarbonyl)oxy]methyl]-[3-[[(2-amino-4-thiazolyl)[[2-[(3,4-dihydroxyphenyl)amino]-2-oxoethoxyimino]acetyl]amino]-2-oxo-1-azetidinesulfonic acid, monopotassium salt

[3S-[3α(Z),4α]]-3-[[(2-Amino-4-thiazolyl)[(carboxymethoxy)imino]acetyl]amino]-4-[[(aminocarbonyl)oxy]methyl]-2-oxo-1-azetidinesulfonic acid (204 mg, 0.4 mmol) was dissolved in 2 ml of dry dimethylformamide and 1 equivalent of p-toluensulfonic acid (78 mg, 0.4 mmol) was added and the mixture stirred for 30 minutes at room temperature. The mixture was added to a dimethylformamide solution containing 4-aminocatechol (prepared by hydrogenating 0.4 mmole of 4-nitrocatechol), followed by the addition of dicyclohexylcarbodiimide (82.5 mg, 0.4 mmole). The reaction was then allowed to stir overnight at ambient temperature. The dimethyl-formamide was removed in vacuo yielding a dark residue which was partially dissolved in 5 ml of water, the pH adjusted to 6.8 with potassium bicarbonate solution, and then filtered to removed the dicyclohexyl urea and palladium on charcoal. The aqueous solution was passed through a 60 ml Dowex K+ ion exchange resin column eluting with water collecting 4.5 ml fractions. Fractions 3–11 were combined and lyophilized to yield 152 mg of crude product. The crude material was purified on a 50 ml HP-20 resin column eluting with water collecting 6 ml fractions. The desired product separated in fractions 19–34 which were combined and lyophilized to yield the title compound as a gray solid, 47 mg.

Analysis calc'd for $C_{18}H_{18}N_7O_8S_2K.5$ mole $H_2O$: C, 33.07; H, 4.32; N, 15.00. Found: C, 32.97; H, 3.58; N, 15.19.

EXAMPLE 5

[3S-[3α(Z),4α]]-2-[[[1-(2-Amino-4-thiazolyl) 2-[(4-methyl-2-oxo-1-sulfo-3-azetidinyl)-amino]-2-oxoethylidene]amino]oxy]-N-(3,4-dihydroxyphenyl)acetamide, monopotassium salt A mixture of [3S-[3α(Z),4α]]-3-[[(2-amino-4-thiazolyl)[(carboxymethoxy)imino]acetyl]amino]-4-methyl-2-oxo-1-azetidinesulfonic acid, dipotassium salt (251.5 mg, 0.52 mmol) and 1 equivalent of p-toluensulfonic acid was stirred in 1.5 ml of dry dimethylformamide under an argon atmosphere, and after stirring for 5 minutes had completely dissolved. The mixture was added to a dimethylformamide solution containing 4-aminocatechol (prepared by hydrogenating 0.52 mmole of 4-nitrocatechol) followed by the addition of dicyclohexylcarbodiimide (107 mg, 0.52 mmol). The reaction was then allowed to stir overnight at ambient temperature. The dimethylformamide was removed in vacuo yielding a dark residue which was partially dissolved in 5 ml of water, the pH adjusted to 6.5 with potassium bicarbonate solution and filtered to remove the dicyclohexylurea and palladium on carbon. The aqueous solution was passed through a 50 ml Dowex K+ ion-exchange column in water collecting 4 ml fractions. Fractions 6 to 14 were combined and lyophilized to yield 94 mg of the title compound as a tan solid.

Analysis cal'd for $C_{17}H_{17}N_6S_2O_9K \cdot 1$ mole $H_2O$: C, 35.78; H, 3.36; N, 14.73. Found C, 35.76; H, 3.60; N, 14.39.

EXAMPLE 6

[3S-[3α(Z),4β]]-3-[[(2-Amino-4-thiazolyl)[[2-[[(3,4-dihydroxyphenyl)methyl]amino]-1,1-dimethyl-2-oxoethoxy]imino]acetyl]amino]-4-methyl-2-oxo-1-azetidine-sulfonic acid

[3S-[3α(Z),4β]]-3-[[(2-amino-4-thiazolyl)-[(1-carboxy-1-methylethoxy)imino]acetyl]amino]-4-methyl--oxo-1-azetidinesulfonic acid (0.435 g, 0.001 mol) was dissolved in 5 ml of dimethylformamide. At room temperature, 4-(aminomethyl)catechol hydrobromide (0.22 g, 0.001 mole), dimethylaminopyridine (0.122 g, 0.001 mole), dicyclohexylcarbodiimide (0.23 g, 0.0011 mole), and triethylamine (0.14 ml, 0.001 mole) were added to the stirred solution. The mixture was stirred overnight at room temperature, and filtered. The filtrate was evaporated in vacuo and the residue triturated with ether to yield 0.8 g of crude material. The crude product was dissolved in a small amount of water, the pH adjusted to 2 by the addition of 2N hydrochloric acid and the solution chromatographed on a column of HP-20. After washing with water, the title compound was eluted with water/acetone (9:1). A total of 0.26 g of crude product was obtained in two batches. Further purification yielded the title compuond, melting point 230° C., dec.

EXAMPLE 7

[3S-[3α(Z),4β]]-3-[[(2-Amino-4-thiazolyl)[[2-[[carboxy(3,4-dihydroxyphenyl)methyl]amino]-1,1-dimethyl-2-oxoethoxy]imino]acetyl]amino]-4-methyl-2-oxo-1-azetidinesulfonic acid, dipotassium salt (A) α-(3,4-Dihydroxyphenyl)glycine, diphenylmethyl ester Into a stirred suspension of 1.83 g (10.0 mmol) of α-(3,4-dihydroxyphenyl)glycine and 1.96 g (10.0 mmol) of toluenesulfonic acid monohydrate (97%) in 5 ml of dry dimethylformamide, a solution of freshly prepared diphenyldiazomethane (2.91 g, 15.0 mmoles) in 10 ml of dimethylformamide was dropped at 50° C. and stirring was continued for 10 minutes. The solvent was evaporated in vacuo, the residue was taken up in ice water/ethyl acetate and the pH was brought to 7.5 by addition of dilute sodium hydroxide. The organic layer was separated, washed with sodium bicarbonate solution and brine, dried (sodium sulfate) and evaporated in vacuo to leave a solid which was stirred with ether. Yield (after filtration and drying in vacuo): 1.89 g, melting point 155°–158° C.

(B)

[3S-[3α(Z),4β]]-3-[[(2-Amino-4-thiazolyl)[[2-[[[[(diphenyl)methyl]oxy]carbonyl](3,4-dihydroxyphenyl)-methyl]amino]-1,1-dimethyl-2-oxoethoxy]-imino]acetyl]amino]-4-methyl-2-oxo-1-azetidinesulfonic acid To a stirred solution of 1.45 g (3.34 mmol) of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, 0.68 g (3.67 mmol) of tributylamine, 0.52 g (3.34 mmol) of hydroxybenzotriazole hydrate and 0.04 g of 4-dimethylaminopyridine in 50 ml of dry dimethylformamide, 0.76 g (3.67 mmol) of dicyclohexylcarbodiimide were added and the mixture was stirred for 30 minutes at room temperature. A solution of 5.0 mmol of silylated α-(3,4-dihydroxyphenyl)glycine, diphenylmethyl ester in 20 ml of dry tetrahydrofuran (prepared by the addition of 2.99 g (15.0 mmol) of N-methyl-N-(trimethylsilyl)trifluoroacetamide to a suspension of 1.75 g (5.0 mmol) of α-(3,4-dihydroxyphenyl)glycine, diphenylmethyl ester in 40 ml of dry acetonitrile and stirring for 30 minutes at room temperature, followed by evaporation in vacuo and dissolving of the residue in 20 ml of dry tetrahydrofuran) was added and stirring was continued overnight. After filtration and evaporation in vacuo, the residue was stirred with 10 ml of methanol for 10 minutes, filtered again and a solution of 1.24 g (3.67 mmol) of potassium perfluorobutanesulfonate in 20 ml of methanol was added. The solution was concentrated in vacuo to 1/5 of its volume and the crude product was precipitated by the slow addition of 30 ml of dry ether, collected by suction, washed with ether/methanol (5:1) and dried in vacuo (2.91 g). The crude material was chromatographed on HP-20 resin eluting with 0–60% aqueous methanol gradient. Freeze drying of the appropriate fractions yielded 1.01 g of product as a mixture of diastereomers; melting point 170°–180° C., dec.

(C)

[3S-[3α(Z),4β]]-3-[[(2-Amino-4-thiazolyl)[[2-[[carboxy(3,4-dihydroxyphenyl)methyl]amino]-1,1-dimethyl-2-oxoethoxy]imino]acetyl]amino]-4-methyl-2-oxo-1-azetidinesulfonic acid, dipotassium salt

[3S-3α(Z),4β]]-3-[[(2-Amino-4-thiazolyl)[[2-[[[[(diphenyl)methyl]oxy]carbonyl](3,4-dihydroxyphenyl]-methyl]amino]-1,1-dimethyl-2-oxoethoxy]imino]acetyl]amino]-4-methyl-2-oxo-1-azetidinesulfonic acid (1.0 g, 1.24 mmol) was added to a −10° C. cold solution of 0.54 ml of anisole in 10 ml of trifluoroacetic acid and stirring was continued for 10 minutes at 0° C. The solvent was evaporated in vacuo, the residue was taken up in ice water/ether and the pH was adjusted immediately to 6.3 by the addition of potassium bicarbonate solution. The aqueous phase was extracted three times with ether and then freeze dried. A chromatographic purification on HP-20 resin with water as eluent yielded, after freeze drying of the appropriate fractions and stirring of the colorless powder obtained with ether, 0.54 g of a yellowish solid, which was sensitive to light; melting point 241° C., dec.

EXAMPLE 8

3S-[3α(Z),4β]]-3-[[(2-Amino-4-thiazolyl)[[2-[[carbamoyl(3,4-dihydroxyphenyl)methyl]amino]-1,1-dimethyl-2-oxoethoxy]imino]acetyl]amino]-4-methyl-2-oxo-1-azetidinesulfonic acid, monopotassium salt (A) N-(t-Butoxycarbonyl)-α-(3,4-dihydroxyphenyl) glycinamide A solution of 2.27 g (11.0 mmol) of dicyclohexylcarbodiimide in 10 ml of dry tetrahydrofuran was dropped into a stirred solution of 2.83 g (10.0 mmol) of N-(t-butoxycarbonyl)-α-(3,4-dihydroxyphenyl)glycine and 1.68 g (11.0 mmol) of hydroxybenzotriazole hydrate in 20 ml of dry tetrahydrofuran. After stirring for 2 hours at room temperature, the precipitate was removed by filtration and 4.15 ml (20.0 mmol) of 1,1,1,3,3,3-hexamethyl-disilazane were dropped into the filtrate and stirring was continued for 0.5 hours at room temperature. After the addition of 4 ml of methanol, the precipitate was filtered off and the filtrate was evaporated in vacuo to leave crude product which was chromatographically purified on silica with ethyl acetate as eluent. After evaporation of the appropriate fractions in vacuo, the residue solidified by stirring with ether. It was collected by suction, washed with ether and dried in vacuo to give 2.23 g of product containing ca. two equivalents of ether; melting point 102°–107° C., dec.

(B) α-(3,4-Dihydroxyphenyl)glycinamide, trifluoroacetate salt

A solution of 1.41 g (5.0 mmol) of N-(t-butoxycarbonyl)-α-(3,4-dihydroxyphenyl) glycinamide in 7 ml of dry dichloromethane was dropped into 25 ml of −10° C. trifluoroacetic acid and the solution was kept for 20 minutes at 0° C. After evaporation in vacuo, the residue crystallized by stirring with 15 ml of dichloromethane yielding 1.47 g of product; melting point: sinters at 182° C., dec.

(C) α-(3,4-Dihydroxyphenyl)glycinamide

N-Methyl-N-(trimethylsilyl)trifluoroacetamide (3.59 ml, 18.37 mmol) was added to a cold stirred suspension of 1.36 g (4.59 mmol) of α-(3,4-dihydroxyphenyl)-glycinamide, trifluoroacetate salt in 15 ml of dry acetonitrile. After stirring for 30 minutes at room temperature, the solution was evaporated in vacuo. The residue was taken up in a few ml of n-hexane, insoluble material was removed by filtration and 0.6 ml of methanol was added. The solution was seeded and stirred overnight (slow crystallization). The crystalline product was collected by suction, washed with n-hexane and dried in vacuo; yielding 0.77 g of product, melting point 104°–110° C., dec.

(D)
[3S-[3α(Z),4β]]-3-[[(2-Amino-4-thiazolyl)[[2-[[carbamoyl(3,4-dihydroxyphenyl)methyl]amino]-1,1-dimethyl-2-oxoethoxy]imino]acetyl]amino]-4-methyl-2-oxo-1-azetidinesulfonic acid, monopotassium salt To a stirred solution of 0.435 g (1.0 mmol) of [3S-[3α(Z),4β]]-3-[[(2-amino-4-thiazolyl)[(1-carboxy-1-methylethoxy)imino]acetyl]amino]-4-methyl-2-oxo-1-azetidinesulfonic acid, 0.262 ml (1.1 mmol) of tributyl-amine, 0.170 g (1.1 mmol) of hydroxybenzotriazole hydrate and 0.06 g (0.05 mmol) of 4-dimethylaminopyridine in 12 ml of dry dimethylformamide, was added 0.23 g (1.1 mmol) of dicyclohexylcarbodiimide and the mixture was stirred for 2 hours at room temperature. The precipitate was filtered off, a solution of 0.22 g (1.2 mmol) of α-(3,4-dihydroxyphenyl)glycinamide in 3 ml of dimethylformamide was added to the filtrate and stirring was continued for 3 to 4 hours. Aftr filtration and evaporation in vacuo, the residue was stirred with 8 ml of methanol, filtered again and a solution of 0.372 g (1.1 mmol) of potassium perfluorobutanesulfonate in 8 ml of methanol was added. The solution was concentrated in vacuo to 1/5 of its volume and the crude product was precipitated by the slow addition of 10 ml of dry ether, collected by suction, washed with ether and dried in vacuo (0.67 g). Chromatography on HP-20 resin eluting with a 0–20 aqueous methanol gradient yielded, after freeze drying of the appropriate fractions, 0.20 g of the title compound as a mixture of diastereomers; melting point: sinters at 200°–220° C.

What is claimed is:

1. A compound having the formula

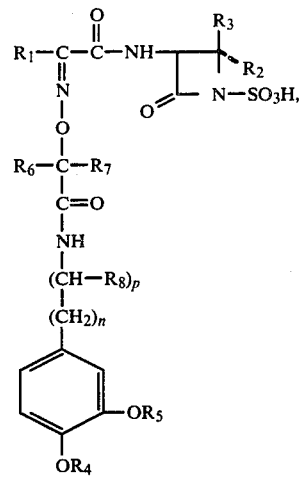

or a pharmaceutically acceptable salt thereof, wherein
$R_1$ is phenyl, substituted phenyl, 2-amino-4-thiazolyl, 5-amino-3-(1,2,4-thiadiazolyl), 2-amino-4-oxazolyl, 2-amino-4-imidazolyl, or 2-amino-6-pyridyl;

$R_2$ and $R_3$ are the same or different and each is hydrogen, alkyl, alkenyl, alkynyl, cycloalkyl, phenyl, substituted phenyl or a 4, 5, 6 or 7-membered heterocycle or one of $R_2$ and $R_3$ is hydrogen and the other is azido, halomethyl, dihalomethyl, trihalomethyl, alkoxycarbonyl, 2-phenylethenyl, 2-phenylethynyl, carboxyl,

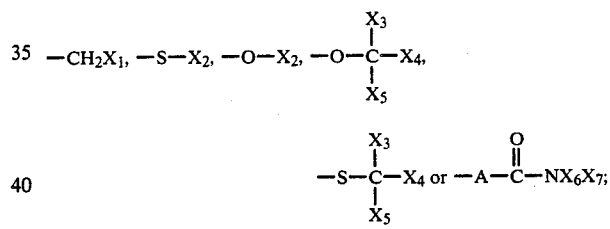

$R_4$ and $R_5$ are the same or different and each is hydrogen or alkanoyl;

$R_6$ and $R_7$ are the same or different and each is hydrogen or alkyl, or $R_6$ and $R_7$ together with the carbon atom to which they are attached are cycloalkyl;

$R_8$ is

wherein $Y_1$ is hydroxy, alkoxy or —$NY_2Y_3$ and $Y_2$ and $Y_3$ are the same or different and each is hydrogen or alkyl;

p is 0 or 1;

n is 0, 1, 2 or 3;

$X_1$ is azido, amino, hydroxy, carboxyl, alkoxycarbonyl, alkanoylamino, phenylcarbonylamino, (substituted phenyl)carbonylamino, alkylsulfonyloxy, phenylsulfonyloxy, (substituted phenyl)sulfonyloxy, phenyl, substituted phenyl, cyano,

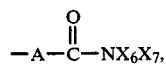

—S—$X_2$, or —O—$X_2$;

$X_2$ is alkyl, substituted alkyl, phenyl, substituted phenyl, phenylakyl, (substituted phenyl)alkyl, alkanoyl, phenyalkanoyl, (substituted phenyl)alkanoyl, phenylcarbonly, (substituted phenyl)carbonyl, or heteroaryl-carbonyl;

one of $X_3$ and $X_4$ is hydrogen and the other is hydrogen or alkyl, or $X_3$ or $X_4$ when taken together with the carbon atom to which they are attached form a cycloalkyl group;

$X_5$ is formyl, alkanoyl, phenylcarbonyl, (subbstituted phenyl)carbonyl, phenylalkylcarbonyl, (substituted phenyl)-alkylcarbonyl, carboxyl, alkoxycarbonyl, aminocarbonyl, (substituted amino)carbonyl, or cyano;

$X_6$ and $X_7$ are the same or different and each is hydrogen, alkyk, phenyl or substituted phenyl, or $X_6$ is hydrogen and $X_7$ is amino, substituted amino, alkanoylamino or alkoxy, or $X_6$ and $X_7$ when taken together with the nitrogen atom to which they are attached form a 4, 5, 6 or 7-membered heterocycle;

A is —CH=CH—, —$(CH_2)_m$—, —$(CH_2)_m$—O—, —$(CH_2)_m$—NH— or —$CH_2$—S—$CH_2$; and m is 0, 1 or 2; and wherein the terms "alkyl" and "alkoxy" refer to groups having 1 to 10 carbon atoms;

the term "cycloalkyl" refers to groups having 3, 4, 5, 6 or 7 carbon atoms;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, mercapto, alkylthio, phenylthio, (substituted phenyl)thio, alkyl-sulfinyl, or alkylsulfonyl groups;

the terms "alkanoyl", "alkenyl" and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbons, alkoxy of 1 to 4 carbons, alkanoyloxy, aminocarbonyl, or carboxy groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thitanyl, piperidinyl, piperazinyl, imidazolidinyl, oxazolidinyl, pyrrolidinyl, tetrahydropyrimidinyl, dihydrothiazolyl, hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups;

the term "heteroaryl" refers to pyridinyl, furanyl, pyrrolyl, thienyl, 1,2,3-triazolyl, 1,2,4,-triazolyl, imidazolyl, thiazolyl, thiadiazolyl, pyrimidinyl, oxazolyl, triazinyl, tetrazolyl or one of the above groups substituted with one or more, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furfurylideneamino, benzylideneamino or substituted alkyl, wherein the alkyl group has 1 to 4 carbon atoms, groups; and the term "substituted amino" refers to a group having the formula —$NX_8X_9$ wherein $X_8$ is hydrogen, alkyl, phenyl, substituted phenyl, phenylakyl or (substituted phenyl)alkyl, and $X_9$ is alkyl phenyl, substituted phenyl, phenylalkyl, (substituted phenyl)alkyl, hydroxy, cyano, alkoxy, phenylalkoxy, or amino.

2. A compound in accordance with claim 1 wherein $R_2$ and $R_3$ are the same or different and each is hydrogen or alkyl.

3. A compound in accordance with claim 1 wherein $R_2$ and $R_3$ are the same or different and each is hydrogen or methyl.

4. A compound in accordance with claim 1 wherein one of $R_2$ and $R_3$ is hydrogen and the other is methyl.

5. A compound in accordance with claim 1 wherein $R_1$ is 2-amino-4-thiazolyl.

6. A compound in accordance with claim 1 wherein n is 0 and p is 0.

7. A compound in accordance with claim 1 wherein n is 0 and p is 1.

8. A compound in accordance with claim 1 wherein n is 1 or 2.

9. A compound in accordance with claim 1 wherein n is 1 and p is 0.

10. A compound in accordance with claim 1 wherein $R_4$ and $R_5$ are each hydrogen.

11. A compound in accordance with claim 1 wherein $R_4$ and $R_5$ are each alkanoyl.

12. A compound in accordance with claim 1 wherein $R_6$ and $R_7$ are each hydrogen.

13. A compound in accordance with claim 1 wherein $R_6$ and $R_7$ are each methyl.

14. A compound in accordance with claim 1 wherein $R_6$ is hydrogen and $R_7$ is methyl.

15. The compound in accordance with claim 1, [3S-[3α(Z),4β]]-2-[[[1-(2-amino-4-thiazolyl)-2-[(4-methyl-2-oxo-1-sulfo-3-azetidinyl)amino]-2-oxoethylidene]amino]oxy]-N-(3,4-dihydroxyphenyl)-2-methylpropanamide.

16. The compound in accordance with claim 1, [3S-[3α(Z),4β]]-2-[[[1-(2-amino-4-thiazolyl)-2-[(4-methyl-2-oxo-1-sulfo-3-azetidinyl)amino]-2-oxoethylidene]amino]oxy-N-(3,4-dihydroxyphenyl)-2-methylpropanamide.

17. The compound in accordance with claim 1, [3S-[3α(Z),4β]]-2-[[[1-(2-amino-4-thiazolyl)-2-[(4-methyl-2-oxo-1-sulfo-3-azetidinyl)amino]-2-oxoethylidene]amino]oxy]-N-(3,4-dihydroxyphenyl)-acetamide.

18. The compound in accordance with claim 1, [3S-[3α(Z),4β]]-4-[[(aminocarbonyl)oxy]methyl]-3-[[(2-amino-4-thiazolyl)[[2-[(3,4-dihydroxy-phenyl)amino]-2-oxoethoxy]imino]acetyl]amino]-2-oxo-1-azetidinesulfonic acid.

19. The compound in accordance with claim 1, [3-S-[3α(Z),4β]]-2-[[[1-(2-amino-4-thiazolyl)-2-[(4-methyl-2-oxo-1-sulfo-3-azetidinyl)amino]-2-oxoethylidenelid]amino]oxy]-N-(3,4-dihydroxyphenyl)-acetamide.

20. The compound in accordance with claim 1, [3S-[3α(Z),4β]]-3-[[(2-amino-4-thiazolyl)[[2-[[(3,4-dihydroxyphenyl)methyl]amino]-1,1-dimethyl-2-oxoethoxy]imino]acetyl]amino]-4-methyl-2-oxo-1-azetidinesulfonic acid.

21. The compound in accordance with claim 1, [3S-[3 α(Z),4β]]-3-[[(2-amino-4-thiazolyl)[[2-[[carboxy(3,4-dihydroxyphenyl)methyl]amino]-1,1-dimethyl-2-oxoethoxy]imino]acetyl]amino]-4-methyl-2-oxo-1-azetidinesulfonic acid.

22. The compound in accordance with claim 1, [3S-[3α(Z),4β]]-3-[[(2-amino-4-thiazolyl)[[2-[[carbamoyl(3,4-dihydroxyphenyl)methyl]amino]-1,1-dimethyl-2-oxoethoxy]imino]acetyl]amino]-4-methyl-2-oxo-1-azetidinesulfonic acid.

* * * * *